US012685587B2

(12) United States Patent
Beeckler

(10) Patent No.: US 12,685,587 B2
(45) Date of Patent: Jul. 21, 2026

(54) CATHETER WITH IMPROVED TEMPERATURE RESPONSE

(71) Applicant: BIOSENSE WEBSTER (ISRAEL) LTD., Yokneam (IL)

(72) Inventor: Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 60 days.

(21) Appl. No.: 18/126,575

(22) Filed: Mar. 27, 2023

(65) Prior Publication Data
US 2023/0225792 A1 Jul. 20, 2023

Related U.S. Application Data

(63) Continuation of application No. 15/793,433, filed on Oct. 25, 2017, now abandoned.

(51) Int. Cl.
*A61B 18/14* (2006.01)
*A61B 18/08* (2006.01)
(Continued)

(52) U.S. Cl.
CPC ........ *A61B 18/1492* (2013.01); *A61B 18/082* (2013.01); *A61B 18/1482* (2013.01); *A61B 2018/00029* (2013.01); *A61B 2018/00095* (2013.01); *A61B 2018/0016* (2013.01); *A61B 2018/00351* (2013.01);
(Continued)

(58) Field of Classification Search
CPC .............. A61B 18/1492; A61B 18/082; A61B 18/1233
See application file for complete search history.

(56) References Cited

U.S. PATENT DOCUMENTS

| | | | |
|---|---|---|---|
| 5,769,847 A | 6/1998 | Panescu et al. | |
| 5,800,432 A | 9/1998 | Swanson | |

(Continued)

FOREIGN PATENT DOCUMENTS

| | | |
|---|---|---|
| CN | 101721246 A | 6/2010 |
| CN | 102793541 A | 11/2012 |

(Continued)

OTHER PUBLICATIONS

Extended European Search Report received for European Application No. 18202318.4, mailed on Mar. 25, 2019, 7 pages.

*Primary Examiner* — Linda C Dvorak
*Assistant Examiner* — Ryan T Clark
(74) *Attorney, Agent, or Firm* — Calderon Safran & Wright P.C.; Etan S. Chatlynne

(57) ABSTRACT

A medical probe, consisting of an insertion tube having a distal end configured for insertion into a body of a patient and containing a lumen having an electrical conductor for conveying electrical energy. The probe also has a conductive cap attached to the distal end of the insertion tube and coupled electrically to the electrical conductor, the cap including a side wall having multiple longitudinal bores therein. There are a plurality of thermocouples disposed in respective ones of the longitudinal bores, and an electrically conductive cement at least partially fills the longitudinal bores so as to secure the thermocouples in the bores while making electrically conductive contact between the thermocouples and the conductive cap.

18 Claims, 3 Drawing Sheets

(51) Int. Cl.
  *A61B 18/00* (2006.01)
  *A61B 18/12* (2006.01)
(52) U.S. Cl.
  CPC ............... *A61B 2018/00577* (2013.01); *A61B 2018/00702* (2013.01); *A61B 2018/00761* (2013.01); *A61B 2018/00797* (2013.01); *A61B 2018/00821* (2013.01); *A61B 18/1233* (2013.01); *A61B 2218/002* (2013.01)

(56)           References Cited

U.S. PATENT DOCUMENTS

| | | | |
|---|---|---|---|
| 6,239,351 | B1 | 5/2001 | Hall, Jr. |
| 6,312,425 | B1 | 11/2001 | Simpson et al. |
| 6,511,478 | B1* | 1/2003 | Burnside ............ A61B 18/1492 |
| | | | 606/41 |
| 9,101,734 | B2 | 8/2015 | Selkee |
| 9,445,725 | B2 | 9/2016 | Govari et al. |
| 10,285,754 | B2 | 5/2019 | Beeckler |
| 10,751,118 | B2* | 8/2020 | Curran ................. A61B 18/148 |
| 2002/0081756 | A1 | 6/2002 | Asahina et al. |
| 2002/0087156 | A1 | 7/2002 | Maguire et al. |
| 2003/0176816 | A1 | 9/2003 | Maguire et al. |
| 2009/0138007 | A1 | 5/2009 | Govari |
| 2011/0224573 | A1 | 9/2011 | Bar-Tal et al. |
| 2011/0230906 | A1 | 9/2011 | Modesitt et al. |
| 2014/0171936 | A1* | 6/2014 | Govari ............... A61B 18/1492 |
| | | | 606/34 |
| 2014/0257130 | A1 | 9/2014 | Cao et al. |
| 2015/0342671 | A1* | 12/2015 | Govari ............... A61B 18/1492 |
| | | | 600/549 |
| 2016/0346045 | A1 | 12/2016 | Sterrett et al. |
| 2017/0265931 | A1 | 9/2017 | Curran et al. |
| 2019/0117298 | A1 | 4/2019 | Beeckler et al. |

FOREIGN PATENT DOCUMENTS

| | | |
|---|---|---|
| CN | 103860255 A | 6/2014 |
| CN | 104665926 A | 6/2015 |
| CN | 105125283 A | 12/2015 |
| CN | 106166059 A | 11/2016 |
| EP | 2526887 A1 | 11/2012 |
| JP | H09140801 A | 6/1997 |
| JP | 2000315568 A | 11/2000 |
| JP | 2004296358 A | 10/2004 |
| JP | 2015100709 A | 6/2015 |
| JP | 2015226768 A | 12/2015 |
| WO | 9600039 A1 | 1/1996 |

* cited by examiner

CATHETER WITH IMPROVED TEMPERATURE RESPONSE

CROSS-REFERENCE TO RELATED APPLICATION

This application is a continuing application of U.S. application Ser. No. 15/793,433, filed Oct. 25, 2017.

FIELD OF THE INVENTION

The present invention relates generally to invasive medical devices, and particularly to probes used in ablating tissue within the body.

BACKGROUND OF THE INVENTION

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis. While creating the necrosis, it is important to estimate the temperature of the tissue to avoid trauma.

The following references refer to measuring temperature.

U.S. Patent Application 2014/0257130, to Cao et al., describes a powered pull wire design for ablation catheters. The application states that a distal end region of the catheters may have a thermocouple junction.

U.S. Patent Application 2003/0176816, to Maguire et al., describes a tissue ablation catheter for forming a lesion along a substantially circumferential region of tissue. The catheter includes one or more sensors for monitoring the temperature of the tissue being ablated.

U.S. Patent Application 2002/0087156, to Maguire et al., describes construction of a tissue ablation catheter for forming a lesion along a substantially circumferential region of tissue wherein a sensor is used for monitoring the temperature of the tissue being ablated.

U.S. Patent Application 2011/0224573, to Bar-Tal et al., describes a probe and an electrode having an outer surface and an inner surface connected to the probe. The apparatus also includes a temperature sensor, protruding from the outer surface of the electrode, which is configured to measure a temperature of a body cavity.

U.S. Pat. No. 5,800,432 to Swanson describes systems and methods for actively cooling ablation electrodes using diodes. A cooled ablation electrode is stated to carry at least one temperature sensing element for sensing actual tissue temperature.

U.S. Patent Application 2011/0230906, to Modesitt et al., describes kits for forming tracts in tissue. The application states that in some variations tissue may be located using thermal sensors.

SUMMARY OF THE INVENTION

An embodiment of the present invention provides a medical probe, including:

an insertion tube having a distal end configured for insertion into a body of a patient and containing a lumen having an electrical conductor for conveying electrical energy;

a conductive cap attached to the distal end of the insertion tube and coupled electrically to the electrical conductor, the cap consisting of a side wall having multiple longitudinal bores therein;

a plurality of thermocouples disposed in respective ones of the longitudinal bores; and an electrically conductive cement at least partially filling the longitudinal bores so as to secure the thermocouples in the bores while making electrically conductive contact between the thermocouples and the conductive cap.

In a disclosed embodiment the electrically conductive cement is thermally conductive. The conductive cap may have a cap thermal conductivity, and the electrically conductive cement typically has a cement thermal conductivity at least 25% of the cap thermal conductivity.

In a further disclosed embodiment the plurality of thermocouples consists of a first electrical conductor having a first composition electrically connected at respective junctions to a multiplicity of second electrical conductors having a second composition. In one embodiment the first electrical conductor and the multiplicity of second electrical conductors are connected together by insulating material.

In a yet further disclosed embodiment the plurality of thermocouples includes a first thermocouple positioned at a distal location in a given longitudinal bore and a second thermocouple positioned at a proximal location in the given longitudinal bore.

Typically, the electrical energy includes radiofrequency energy for ablating tissue in the body of the patient.

There is further provided, according to an embodiment of the present invention, a method, including:

providing an insertion tube having a distal end configured for insertion into a body of a patient and containing a lumen having an electrical conductor for conveying electrical energy;

attaching a conductive cap to the distal end of the insertion tube and coupling the cap electrically to the electrical conductor, the cap consisting of a side wall having multiple longitudinal bores therein;

disposing a plurality of thermocouples in respective ones of the longitudinal bores; and at least partially filling the longitudinal bores with an electrically conductive cement so as to secure the thermocouples in the bores while there is electrically conductive contact between the thermocouples and the conductive cap.

The present invention will be more fully understood from the following detailed description of the embodiments thereof, taken together with the drawings in which:

DETAILED DESCRIPTION OF EMBODIMENTS

Overview

Figure 1:
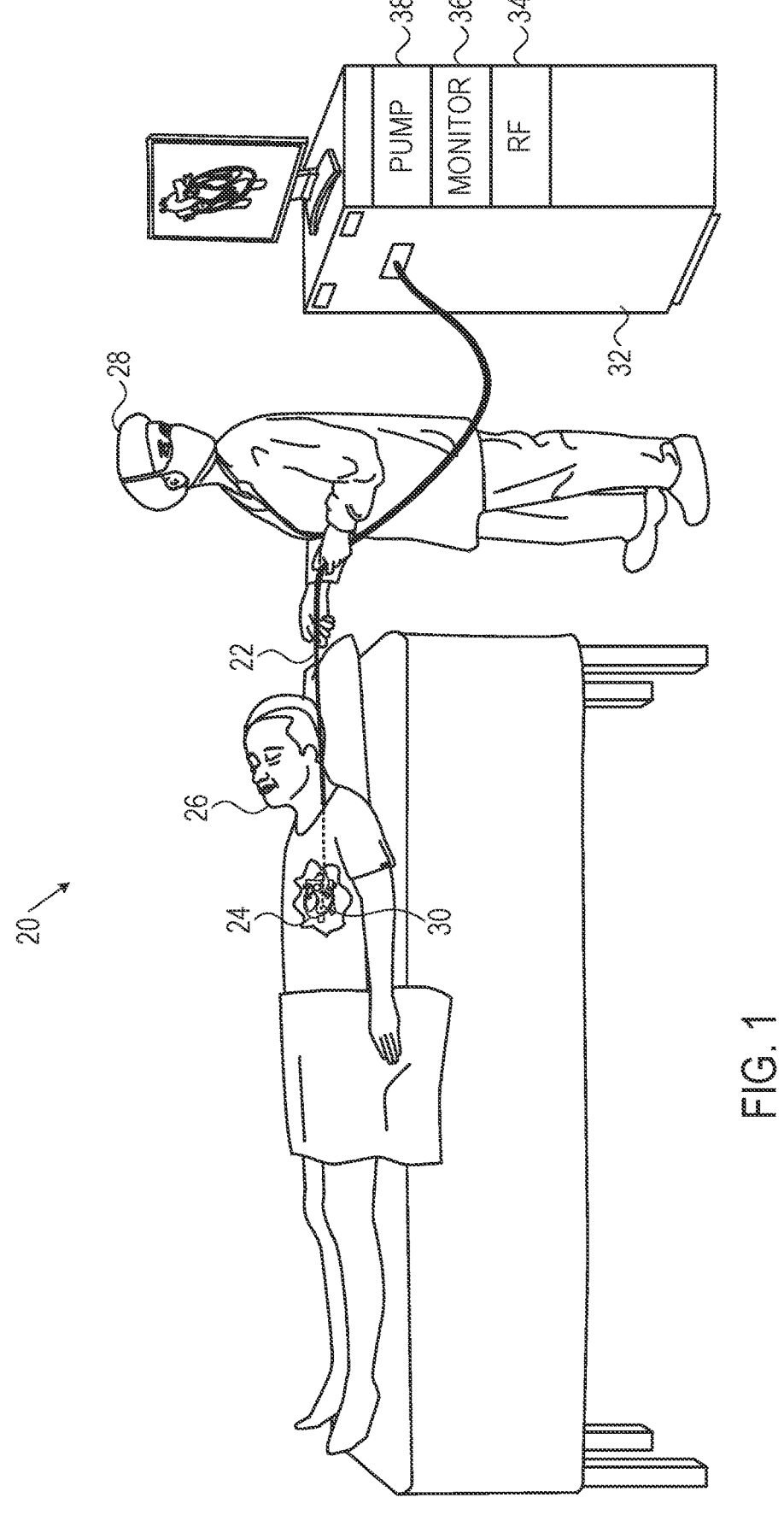
FIG. 1 is a schematic, pictorial illustration of a system for intracardiac ablation, in accordance with an embodiment of the present invention.

Intracardiac ablation procedures are characterized by rapid temperature changes and non-uniform temperature distribution in the tissue and its vicinity. Therefore, the temperature measured by a sensor at the tip of an ablation catheter may not accurately reflect the actual, current temperature in the tissue. The inventors have found this occurs when ablation is performed with low contact forces and at low ablation powers. In these cases, the inventors believe that the sensors read the temperature of the blood pool rather than the tissue.

Embodiments of the present invention that are described hereinbelow provide ablation electrodes with embedded thermocouples, acting as temperature sensors, that provide accurate tissue temperature assessment. Such electrodes typically comprise a conductive cap, which is attached to the distal tip of the insertion tube of an invasive probe, such as a cardiac catheter. Typically, a cooling fluid flows out through an array of perforations in the electrode to irrigate the tissue under treatment.

The thermocouples are embedded in thermally conductive cement in bores within the electrode, so that they are at different locations in proximity to the outer surface of the electrode. The thermocouples are thus in proximity to and are in thermal communication with the outer surface. The thermocouples thus provide multiple temperature readings at different locations on the tip electrode.

Typically, the thermocouple that gives the highest temperature reading is the one that is in best contact with the tissue being ablated, and this thermocouple is typically the most distal of the cap. The temperature measured by this thermocouple varies linearly with the actual tissue temperature. (Flow of the cooling fluid through the perforations in the electrode is generally lowest in areas that are in firm contact with the tissue, and the sensors in these areas typically give the highest temperature readings.) The reading from this hottest thermocouple may thus be used in particular to monitor the tissue temperature and control the applied power and duration of the ablation procedure in order to obtain the desired therapeutic result without excessive tissue damage. Alternatively or additionally, the temperature readings of the multiple thermocouples can be combined and interpolated to give a map of temperature over the area of the catheter tip.

In addition to the cement used to embed the thermocouples being thermally conductive, the cement is also configured to be electrically conductive. Having the cement electrically conductive typically allows for higher values of thermal conductivity. It additionally guarantees by design that the thermocouples are electrically connected to each other and to the conductive cap by essentially zero resistance. This allows for the thermocouple reading circuit to have a consistent electrical specification (i.e. all thermocouples are electrically connected to each other and the conductive cap). If a non-conductive epoxy were used, and the distal thermocouple was not bottomed out in its bore as by design, then the thermocouples would be electrically isolated from the conductive cap which could provide unintended consequences in the thermocouple reading circuit. The intended shorting of the thermocouples to the cap, and therefore to each other, also eliminates the need to electrically insulate the solder joints to eliminate the possibility of them shorting to the inner wall of the hole.

Although the disclosed embodiments relate specifically to intracardiac catheters and ablation procedures, the principles of the present invention may similarly be applied, mutatis mutandis, to probes of other types, for use in substantially any sort of invasive thermal treatment.

DETAILED DESCRIPTION

FIG. 1 is a schematic pictorial illustration of a system 20 for cardiac ablation treatment, in accordance with an embodiment of the present invention. An operator 28 (such as an interventional cardiologist) inserts a catheter 22 via the vascular system of a patient 26 into a chamber of the patient's heart 24. For example, to treat atrial fibrillation, the operator may advance the catheter into the left atrium and bring a distal end 30 of the catheter into contact with myocardial tissue that is to be ablated.

Catheter 22 is connected at its proximal end to a console 32, which is controlled by operator 28 to apply and monitor the desired treatment. Console 32 comprises an RF energy generator 34, which supplies electrical power via catheter 22 to distal end 30 in order to ablate the target tissue. Monitoring circuitry 36 tracks the temperature of the tissue at distal end 30 by processing the outputs of temperature sensors in the distal end, as described below. An irrigation pump 38 supplies a cooling fluid, such as saline solution, through catheter 22 to irrigate distal end 30. On the basis of information provided by monitoring circuitry 36, console 32 may control the power applied by RF energy generator 34 and/or the flow of fluid provided by pump 38, either automatically or in response to inputs by operator 28.

System 20 may be based, for example, on the CARTO® integrated mapping and ablation system produced by Biosense Webster Inc., of Irvine, CA. This system provides extensive facilities to support navigation and control of catheter 22. These system facilities, however, including details of the monitoring and control functions of monitoring circuitry 36 and console 32 generally, are beyond the scope of the present patent application.

Figure 2A:
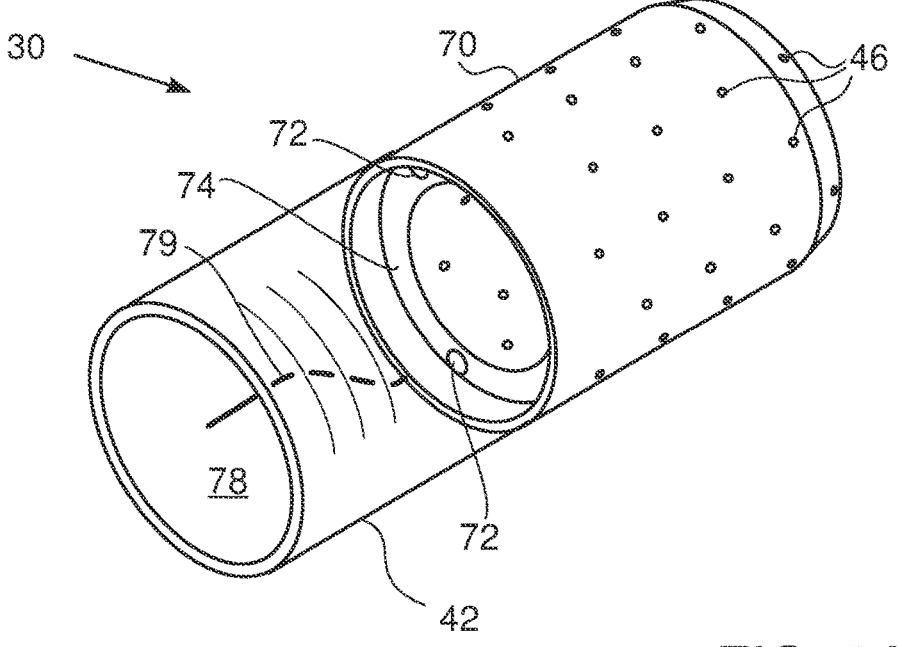
FIG. 2A is a schematic, pictorial illustration of a catheter cap, in accordance with an embodiment of the present invention.
Figure 2B:
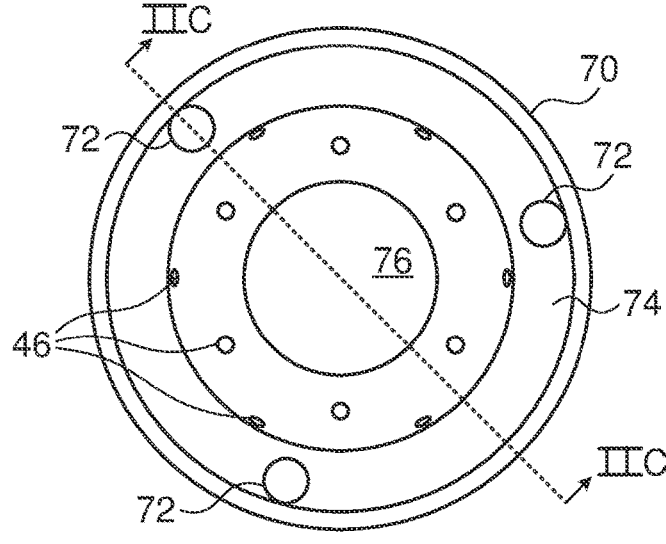
FIG. 2B is a schematic end view of the catheter cap of FIG. 2A, in accordance with an embodiment of the present invention.
Figure 2C:
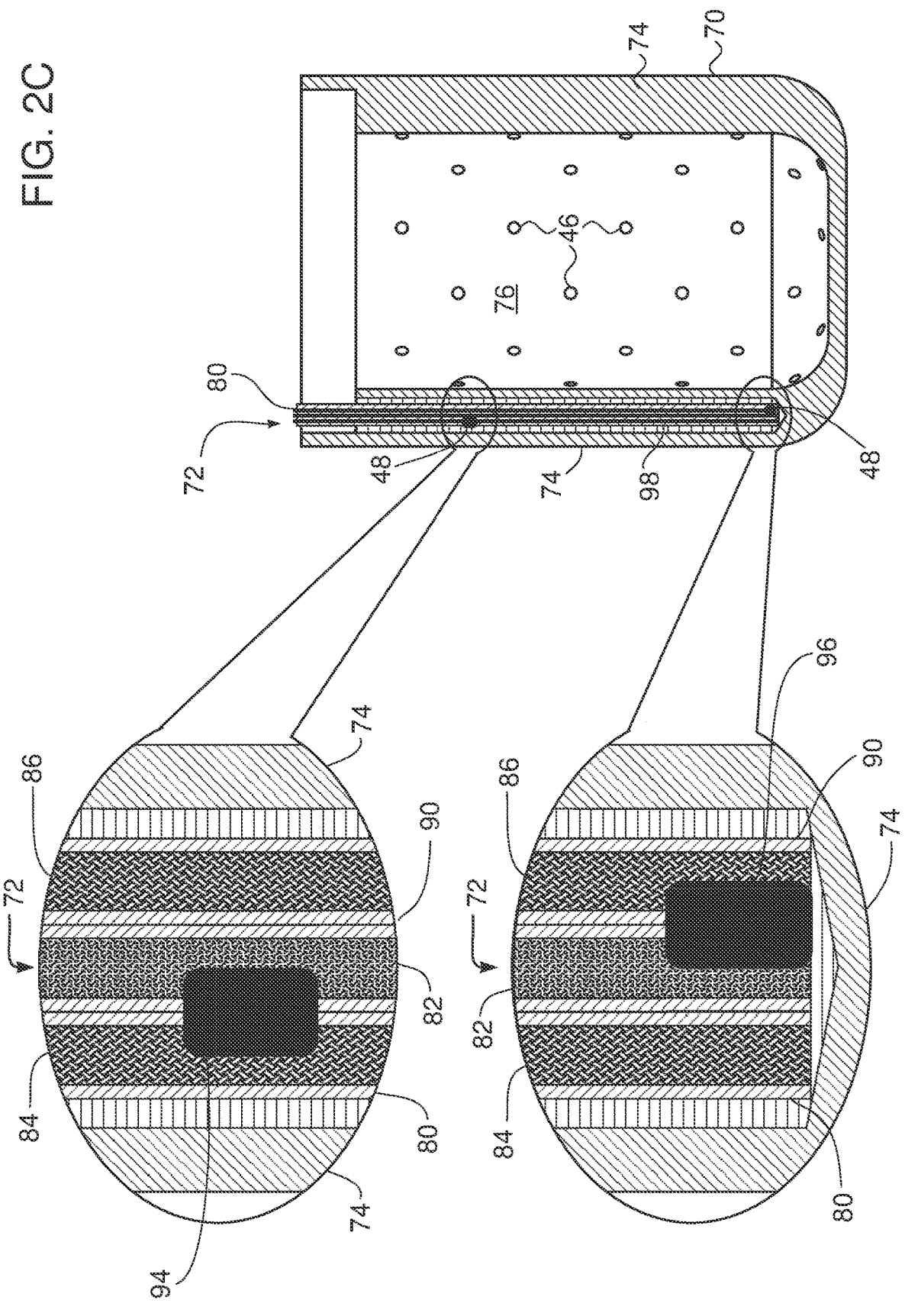
FIG. 2C is a schematic, sectional view of the catheter cap of FIGS. 2A and 2B, in accordance with an embodiment of the present invention.

FIGS. 2A-2C schematically illustrate distal end 30 of catheter 22, in accordance with an embodiment of the present invention. An insertion tube 42 extends along the length of the catheter and is connected at its distal end to a conductive cap 70. FIG. 2A is a schematic, pictorial illustration of cap 70 and a portion of tube 42, while FIG. 2B is a schematic end view showing the interior of the cap, and FIG. 2C is a sectional view taken along the line IIC-IIC in FIG. 2B.

Typically, insertion tube 42 comprises a flexible, biocompatible polymer, while cap 70 comprises a biocompatible metal suitable to serve as an ablation electrode, such as gold, palladium, platinum, or an alloy of these metals, for example. Cap 70 is perforated by an array of irrigation apertures 46, which open from the outer surface of the cap into an inner cavity 76 within the cap. For typical intracardiac ablation applications, the diameter of cap 70 may be about 2.5 mm, with apertures 46 of diameter in the approximate range 0.05-0.2 mm. The above dimensions and materials are described by way of example, however, and other suitable materials, with features of larger or smaller dimensions, may similarly be used.

Cavity 76 is in fluid communication with a lumen 78 which runs through the length of insertion tube 42. The lumen is coupled at its proximal end to irrigation pump 38, and thus conveys irrigation fluid to cavity 76, from which the fluid flows out through apertures 46. An electrical conductor 79 conveys electrical energy from RF generator

34, through lumen 78 of insertion tube 42, to cap 70, and thus energizes the cap to ablate myocardial tissue with which the cap is in contact. During ablation, the fluid flowing out through apertures 46 irrigates the tissue under treatment.

Temperature sensors 48, described in more detail below, are mounted within conductive cap 70 at locations that are arrayed around the distal tip of the catheter, both axially and circumferentially. In this example, cap 70 contains six sensors, with one group in a distal location, close to the end of the tip, and the other group in a more proximal location. This distribution is shown only by way of example, however, and greater or smaller numbers of sensors may be mounted in any suitable locations within the cap. In the description herein sensors 48 are assumed to comprise thermocouples, and are also referred to as thermocouples 48.

Cap 70 comprises a side wall 74 that is relatively thick, on the order of 0.4 mm thick, in order to provide sufficient space for temperature sensors 48, and the sensors 48 are mounted within longitudinal bores 72 in side wall 74. For clarity, FIGS. 2A and 2B only show bores 72 and do not show the sensors within the bores, or how the sensors are structured. FIG. 2C shows two sensors 48 mounted in one bore 72, and in the example described herein the other two bores 72 each have two sensors mounted therein, the two sensors in each bore being substantially similar to the two sensors of FIG. 2C. The structure of the sensors is described below.

A pair of sensors 48 in a given bore 72 comprises one distal sensor 48 and one proximal sensor 48. Each pair of sensors 48 is formed from a trifilar assembly 80, comprising a constantan wire 82 and two copper wires 84, 86. The wires are separated by insulating material 90, typically thin enamel coating the wires, that physically connects the wires so that they form the trifilar assembly. In this figure proximal sensor 48 is formed as a copper-constantan thermocouple junction by exposing adjacent regions of copper wire 84 and constantan wire 82, and soldering the two exposed regions with a solder bead 94. Distal sensor 48 is formed as a copper-constantan thermocouple junction by exposing adjacent regions of copper wire 86 and constantan wire 82, and soldering the two exposed regions with a solder bead 96.

Once the pair of sensors has been formed, bore 72 is filled with a cement 98 that is thermally and electrically conductive. Cement 98 typically comprises an epoxy resin, and in one embodiment Epo-tek EK2000 epoxy resin, produced by EPOXY TECHNOLOGY, INC. of Billerica, MA, is used. Assembly 80 is inserted into the filled bore, so that distal sensor 48 bottoms out in the bore, and the epoxy is allowed to cure in an oven. Once cured, each sensor 48, since it comprises a bare solder bead 94 or bead 96, is embedded in cement 98 and is in thermal and electrical contact with wall 74. It will be appreciated that producing sensors 48 using trifilar assembly 80 facilitates assembly of the multiple sensors within respective bores 72.

In one embodiment cap 80 is an 80% Pd 20% Pt alloy having a thermal conductivity of approximately 40 W/(m·K). In an alternative embodiment cap 80 is a 90% Pt 10% Ir alloy having a thermal conductivity of approximately 32 W/(m·K). Typically the thermal conductivity of the cured cement is configured to be at least 25% of the thermal conductivity of cap 80.

The implementation described above allows distal sensor 48, i.e. the lower sensor in FIG. 2C, to be very close to the distal end of cap 70. This, together with the fact that the sensor is in thermal contact with the tip wall, means that the sensor reading corresponds to the temperature of the material, such as blood or tissue, contacted by the tip wall.

In some embodiments, rather than the thermally and electrically conductive epoxy referred to above being used, an epoxy that is only thermally conductive, such as one doped with boron nitride and/or synthetic diamond, is used.

Typically, distal end 30 contains other functional components, which are outside the scope of the present disclosure and are therefore omitted for the sake of simplicity. For example, the distal end of the catheter may contain steering wires, as well as sensors of other types, such as a position sensor and/or a contact force sensor. A catheter containing sensors of these sorts is described, for example, in U.S. Patent Application Publication 2009/0138007.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical probe, comprising:
an insertion tube having a distal end configured for insertion into a body of a patient and containing a first lumen having an electrical conductor for conveying electrical energy;
a conductive cap attached to the distal end of the insertion tube and coupled electrically to the electrical conductor, wherein the conductive cap includes a longitudinal cylindrical bore extending through a thickness of a wall of the conductive cap;
a trifilar assembly fitted within the bore, wherein the trifilar assembly consisting of:
three wires extending longitudinally within the bore, each insulated with insulating material, wherein the insulating material of the three wires are physically connected along a length to form the trifilar assembly;
a first thermocouple junction at a first position within the bore and along the length of the three wires formed by exposing a first wire and a second wire of the three wires at the first position and soldering the first and second wires together at the first position; and
a second thermocouple junction at a second position within the bore and along the length of the three wires formed by exposing a third wire and the second wire of the three wires at the second position and soldering the third and second wires together at the second position, wherein the first position is other than the second position.

2. The medical probe of claim 1, wherein the second wire is a constantan wire.

3. The medical probe of claim 1, wherein each of the first wire and the third wire are copper wires.

4. The medical probe of claim 1, wherein the insulating material is enamel coating each of the three wires and wherein the insulating material of each of the three wires is physically connected to form a solid structure.

5. The medical probe of claim 1, wherein the longitudinal cylindrical bore is filled with cement.

6. The medical probe of claim 5, wherein the cement is both thermally and electrically conductive.

7. The medical probe of claim 1, wherein the first thermocouple junction is formed at a distal end of the trifilar assembly.

8. The medical probe of claim 7, wherein the trifilar assembly is inserted into the longitudinal cylindrical bore so that the first thermocouple junction bottoms out in the longitudinal cylindrical bore.

9. The medical probe of claim 7, comprising inserting the trifilar assembly into the longitudinal cylindrical bore so that the first thermocouple junction bottoms out in the longitudinal cylindrical bore.

10. The medical probe of claim 1, wherein the conductive cap is perforated to form an array of irrigation apertures and wherein irrigation fluid is delivered through the irrigation apertures with fluid pumped into a second lumen that that extends through the insertion tube.

11. A method for constructing a *medica* probe, the method comprising:

forming a longitudinal cylindrical bore extending through a thickness of a wall of a conductive cap that is configured to be attached to a distal end of an insertion tube configured for insertion into a body of a patient, wherein the insertion tube contains a first lumen having an electrical conductor for conveying electrical energy;

constructing a trifilar assembly consisting of:

three wires extending longitudinally with the bore, each insulated with insulating material, wherein the insulating material of the three wires are physically connected along a length to form the trifilar assembly;

forming a first thermocouple junction at a first position within the bore and along the length of the three wires by exposing a first wire and a second wire of the three wires each at the first position and soldering the first and second wires together at the first position;

forming a second thermocouple junction at a second position within the bore and along the length of the three wires by exposing a third wire and the second wire of the three wires each at the second position and soldering the third and second wires together at the second position, wherein the first position is other than the second position; and inserting the trifilar assembly within the longitudinal cylindrical bore.

12. The method of claim 11, wherein the second wire is a constantan wire and each of the first wire and the third wire are copper wires.

13. The method of claim 11, comprising coating each of the three wires with enamel coating to form the insulating material.

14. The method of claim 11, comprising filling the longitudinal cylindrical bore with cement.

15. The method of claim 14, wherein the cement is both thermally and electrically conductive.

16. The method of claim 14, comprising curing the cement in an oven with the trifilar assembly embedded within the cement.

17. The method of claim 11, comprising forming the first thermocouple junction is at a distal end of the trifilar assembly.

18. The method of claim 11, wherein the conductive cap is perforated to form an array of irrigation apertures and wherein irrigation fluid is delivered through the irrigation apertures with fluid pumped into a second lumen that that extends through the insertion tube.

* * * * *